(12) United States Patent
Kriz

(10) Patent No.: US 6,706,160 B2
(45) Date of Patent: Mar. 16, 2004

(54) CHEMICAL SENSOR AND USE THEREOF

(75) Inventor: Dario Kriz, Malmö (SE)

(73) Assignee: Chemel AB, Lund (SE)

( * ) Notice: Subject to any disclaimer, the term of this patent is extended or adjusted under 35 U.S.C. 154(b) by 0 days.

(21) Appl. No.: 09/803,846

(22) Filed: Mar. 12, 2001

(65) Prior Publication Data

US 2001/0023832 A1 Sep. 27, 2001

Related U.S. Application Data

(63) Continuation of application No. 08/860,117, filed on Jun. 19, 1997, now Pat. No. 6,214,206.

(30) Foreign Application Priority Data

Jan. 3, 1995 (SE) ................................................ 9500020

(51) Int. Cl.⁷ ...................... G01N 27/327; G01N 27/404
(52) U.S. Cl. ............. 204/415; 204/403.01; 204/403.06; 204/403.07; 204/403.09; 204/403.1; 204/403.14; 205/778; 205/782
(58) Field of Search .................................. 204/403, 415, 204/403.01, 403.06, 403.07, 403.09, 403.1, 403.14; 205/777.5, 778, 782, 782.5, 783, 787, 787.5

(56) References Cited

U.S. PATENT DOCUMENTS

| | | | | |
|---|---|---|---|---|
| 3,208,926 A | * | 9/1965 | Zckfeldt | |
| 3,539,455 A | * | 11/1970 | Clark | |
| 3,707,455 A | * | 12/1972 | Derr et al. | |
| 4,024,042 A | * | 5/1977 | Enfors et al. | |
| 4,533,456 A | * | 8/1985 | Kratochvil et al. | |
| 4,986,271 A | * | 1/1991 | Wilkins | |

OTHER PUBLICATIONS

Design and Response Characteristics of an Enzyme Electrode for Measurement of Penicillin in Fermentation Broth, Enzyme Microb. Technol. 1979, vol. 1, Oct., pp. 260–264.

* cited by examiner

Primary Examiner—T. Tung
(74) Attorney, Agent, or Firm—Cooper & Dunham LLP

(57) ABSTRACT

A chemical sensor selectively detects an analyte in a solution. The sensor comprises a flow-through chamber, a selective membrane, a transducer, an inlet for a liquid flow containing a recognition element, and an outlet. To detect an analyte in a solution, a recognition element is contacted with the solution containing the analyte via a selective membrane. This results in a response detectable by a transducer. The recognition element is injected into a flow, and the flow is passed into a flow-through chamber comprising the transducer and the selective membrane, where it contacts the analyte passing from the solution outside the chamber. The recognition element and the analyte interact to provide a signal that is detected by the transducer. The chemical sensor is used for detecting analyte(s) in a reactor system, a flow system or in an in vivo system.

6 Claims, 3 Drawing Sheets

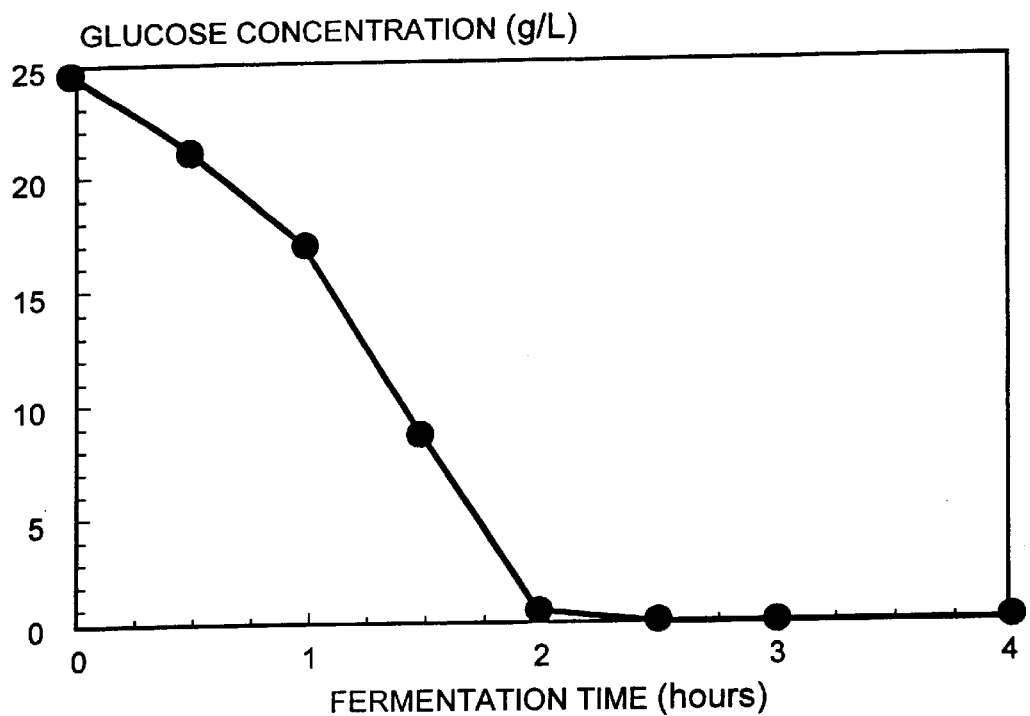
F I G. 5
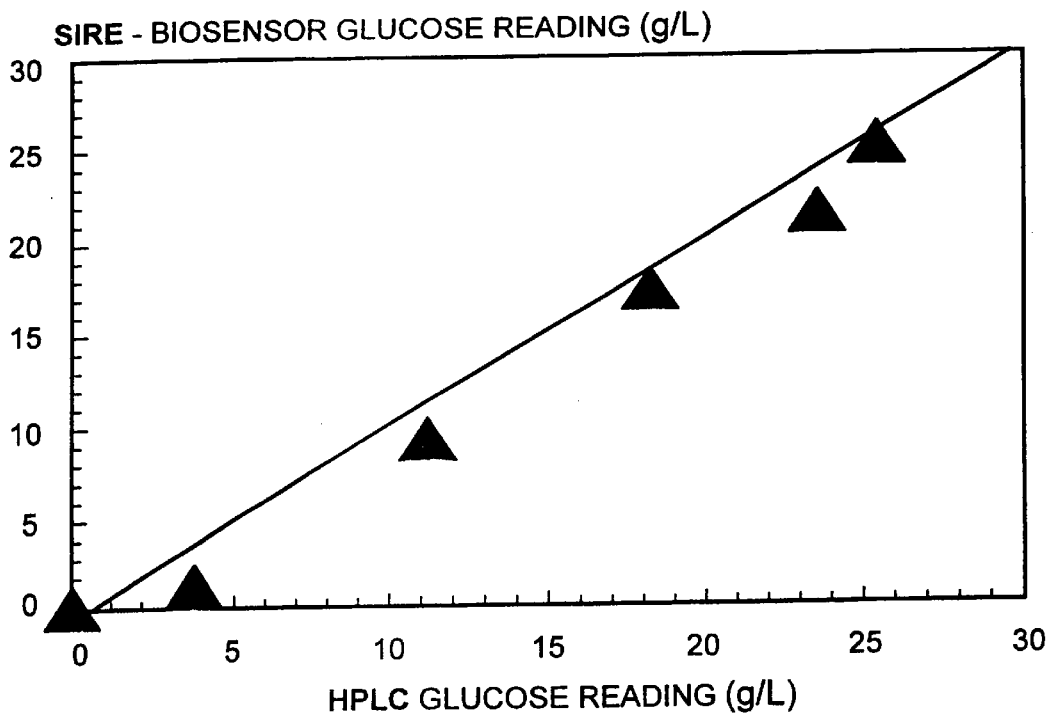
F I G. 6

CHEMICAL SENSOR AND USE THEREOF

This application is a continuation of application Ser. No. 08/860,117, filed Jun. 19, 1997, now U.S. Pat. No. 6,214,206.

The present invention comprises a chemical sensor for selectively detecting an analyte in a solution, a method of selectively detecting an analyte in a solution, and use of the chemical sensor.

A chemical sensor is a device which selectively detects a target molecule (analyte) in a complex medium (the sample solution) and provides an output signal which is proportional to the concentration of the studied analyte. A chemical sensor consists of two neighbouring components, the so-called recognition element and the transducer component. The function of the recognition element is to selectively bind to the analyte located in the sample solution. In binding, this or subsequent chemical events should be converted into a quantifiable electric output signal of the transducer component. A large number of combinations of different recognition elements and transducer components have previously been reported[1, 2, 3]. The classification of the recognition element can be effected on the basis of a biologic or non-biologic origin, and if it has catalytic or non-catalytic properties (see Table 1). The transducer component is based on different operating principles which can be of electrochemical, optical, magnetic, acoustic/piezoelectric or thermometric nature.

The capacity of a chemical sensor can be described by parameters, such as selectivity, sensibility, stability, response time and re-usability. A large number of different sensor concepts have been presented, of which the so-called biosensors have shown very promising properties in respect of selectivity and sensibility to a large number of analytes. Unfortunately, the stability is not good owing to their function being based on recognition elements of biological origin.

Enfors, S—O and Nilsson, H, 1979 (4) described a biosensor with a manually exchangeable recognition element. This biosensor is operated by injecting a solution of an enzyme into the biosensor. The response is measured as a pH signal. A large excess of enzyme solution must be used. In order to get a relevant value of the pH response, the authors state that the solution must be kept still in the biosensor. Slow regeneration is expected because the analyte and the formed enzymatic products have to diffuse out from the biosensor prior to new measurments can be initiated. Furthermore, there must be introduced a second transducer component in the system, that is a pH electrode measuring the pH of the surrounding sample solution.

GBF, Scientific Annual Report 1990, pp 62–63 and 126–127, Biosensors for Pesticides in Water, describes a biosensor based on a liquid flow, into which different substrates are injected. The flow is passing a selective membrane reactor, in which antibodies are immobilised. Thus, this biosensor is based on a flowing analyte detected by a stationary recognition element.

Various approaches in Flow Injection Analysis (FIA) require sample pretreatment, have possible contamination of the flow-through system/detector, operation in harsh chemical environments not possible, no on-line or in situ monitoring is possible, samples must be taken (Ruzicka, J. & Hansen, E. T. 'Flow Injection Analysis', John Wiley & Sons, NY, 1981).

In one aspect of the present invention, there is provided a new type of chemical sensor.

In another aspect of the present invention, there is provided a method of selectively detecting an analyte in a solution.

In yet another aspect of the present invention, there is provided the use of the sensor according to the invention for different applications.

BRIEF DESCRIPTION OF THE DRAWINGS

The invention will now be described in more detail with reference to the accompanying drawings, in which

FIG. 5 is a graph showing the glucose concentration in a fermenter as a function of the fermentation time, measured on undiluted samples using a biosensor according to the invention;

FIG. 6 is a graph showing a comparison of results obtained by a biosensor according to the invention (on undiluted samples) and results obtained by HPLC analysis (on diluted samples).

Figure 1:
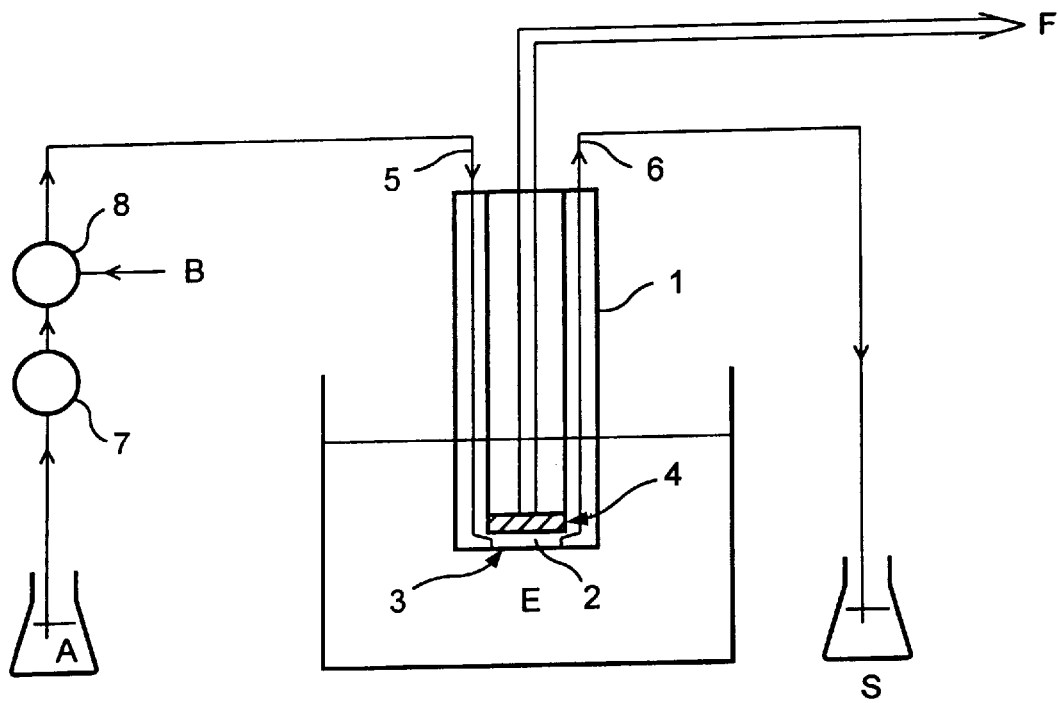
FIG. 1 is a schematic view of an embodiment of the chemical sensor according to the invention.

According to the first aspect of the invention, there is provided a chemical sensor 1 for selectively detecting an analyte in a solution, which comprises a flow-through chamber 2, a selective membrane 3, transducer means 4, an inlet 5 for a liquid flow containing a recognition element, and an outlet 6.

In its second aspect, the invention provides a method of selectively detecting an analyte in a solution, wherein a recognition element is contacted with the solution containing the analyte via a selective membrane, said contact resulting in a response detectable by transducer means, whereby the recognition element is injected into a flow, the flow is passed into a flow-through chamber comprising the transducer means and the selective membrane, where it is contacted with the analyte passing from the solution outside the selective membrane, whereby the recognition element and the analyte interact to provide a signal which is detected by the transducer means.

In the third aspect of the invention, there is provided the use of the chemical sensor for detecting of analyte(s) in a reactor system, a flow system or in an in vivo system.

When, in the present invention, the recognition element is of biological origin, there is created a biosensor of a totally new type, showing an up to now not seen, but very important stability together with the promising characteristics shown by prior art biosensors, such as selectivity and sensibility to a great variety of analytes.

In addition to the above properties, the invention offers the following beneficial new features and advantages compared to known chemical sensors, due to the invention being based on injection of the recognition element into the biosensor. Thus, the analyses would be more rapid and the times of response shorter, and in addition it will be possible to control the risks of contamination and deactivation of the recognition element. The reason for this is that the measurement process is dynamic, which allows initial changes to be put in relation to the concentration of analyte in the sample solution, and that there is no need for the recognition element to be regenerated. The invention also allows sequential detection of several analytes with one and the same transducer means. It also permits differential measurements with and without recognition elements in order to reduce the effect of interfering compounds.

All these new features and advantages will be of great economic importance and will give opportunities for new applications in the industrial, medical and research fields.

The invention can be used for detecting of analyte(s) in a reactor system, a flow system or in an in vivo system. It can also be used for on line and/or in situ measurements, and for measurements at high temperatures and in harsh chemical environments, such as at high or low pH values, high salt concentrations and/or in the presence of denaturating substances. A further use of the invention is for differential measurements with and without a recognition element.

As transducer means, use can be made of an electrochemical, optical, magnetic, acoustic/piezoelectric or thermometric transducer, or a combination thereof.

In an especially preferred embodiment, the transducer means is an amperometric transducer. In another preferred embodiment, the transducer means is a pH transducer.

Preferred selective membranes for use in the invention are dialysing membranes, ion exchange membranes, gas permeable membranes, analyte selective membranes and group or single analyte selective hindering membranes.

The chemical sensor according to the invention can also comprise means for pumping the flow into the flow-through chamber and means for injecting the recognition element into the flow.

In another preferred embodiment, the chemical sensor is arranged for detecting biological analyte(s) using as a recognition element a catalytic or non-catalytic substance of biological origin. Other types of recognition elements are set forth in the following table:

TABLE 1

Examples of different types of recognition elements for use in chemical sensors[3].

|  | Catalytic | Non-catalytic |
| --- | --- | --- |
| Biological origin | Enzymes, Micro-organisms, Abzymes, Organelles, Tissue | Proteins (Con A), Antibodies, Receptors, DNA |
| Non-biological and/or artificial origin | Artificial enzymes | Solid state, Ion-exchange and Neutral carrier membranes, Oxides, Conducting polymers, Molecularly imprinted polymers |

Specific examples of enzymes for use as recognition elements are oxidases, dehydrogenases and hydrolases.

The measurements can be performed either by passing the recognition element continuously through the flow-through chamber or by keeping it stationary in the flow-through chamber during the detection.

A special advantage of the invention is the possibility of simple and rapid regeneration of the transducer means and/or the selective membrane by passing a buffer or washing solution through the chamber for as short a period as a few minutes. Electrochemical transducers can also be regenerated using as electro-cleaning procedure, i.e. sweeping the working electrode potential between extreme values (for instance +2V). This is due to the fact that the recognition element is injected into the flow in contrast to being immobilised. Another great advantage of this is that very small amounts of recognition elements are required. Thus, only a volume of the solution of e.g. an enzyme, used as recognition element, in the order of 1–100 $\mu l$ is necessary.

The invention relates to a new type of chemical sensors 1, whose operating principle is based on the recognition element being injectible (FIG. 1). A buffer solution A is pumped by means of a pump 7, placed either on the inlet (5) side or on the outlet (6) and thus working in a suction mode, through the injector 8. The recognition element B is injected into the buffer solution and entrained into the space between the transducer means 4 and a selective membrane 3. The other side of the selective membrane is in contact with the sample solution E. The analyte can pass through this membrane and interact with the recognition element, this chemical process being converted by the transducer means into an electric output signal F which is proportional to the concentration of the analyte in the sample solution. The liquid flow is finally collected in a waste container S.

The construction also allows a multisensor function by a sequence of different recognition elements B1, B2, B3 . . . being injectible, a sequential detection of various analytes in a sample solution being effected. In addition, a mixture of enzymes could be injected where each enzyme gives a specific response (pH, $H_2O_2$, coloured products . . . ) which can be detected by one of the transducers used. Moreover, other substances, such as reagents, mediators, indicators and stabilisers can be present together with the recognition element between the transducer means and the selective membrane. A washing solution can periodically be allowed to pass between the transducer means and the selective membrane such that a quick regeneration thereof can be effected.

The invention can be used for detection in reactor systems, closed or open containers (such as fermenters) or in flow systems (also in in vivo applications) of one or more analytes.

Figure 2:
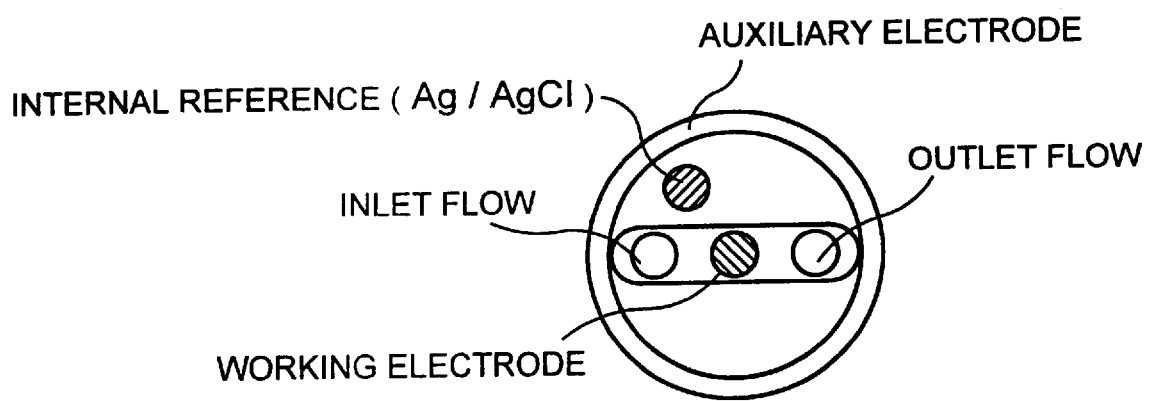
FIG. 2 is a cross-section of an amperometric transducer, adapted for use in a biosensor according to the invention.

In a preferred embodiment of the invention, there is used an amperometric transducer for detecting the analyte. An example of such a transducer for use in a biosensor according to the invention, designed to measure in a potentiostatic three-electrode system, is shown in FIG. 2. The transducer comprises a platinum wire acting as the working electrode, a stainless steel auxiliary electrode, and an external Ag/AgCl reference electrode. The sensor also has an internal reference electrode, consisting of a 1 mm diameter silver wire, covered with Ag/AgCl.

The following examples are given only as illustrative examples of embodiments of the invention, and are not to be construed as limiting the invention, such as it is defined in the accompanying claims.

EXAMPLE 1

Figure 3:
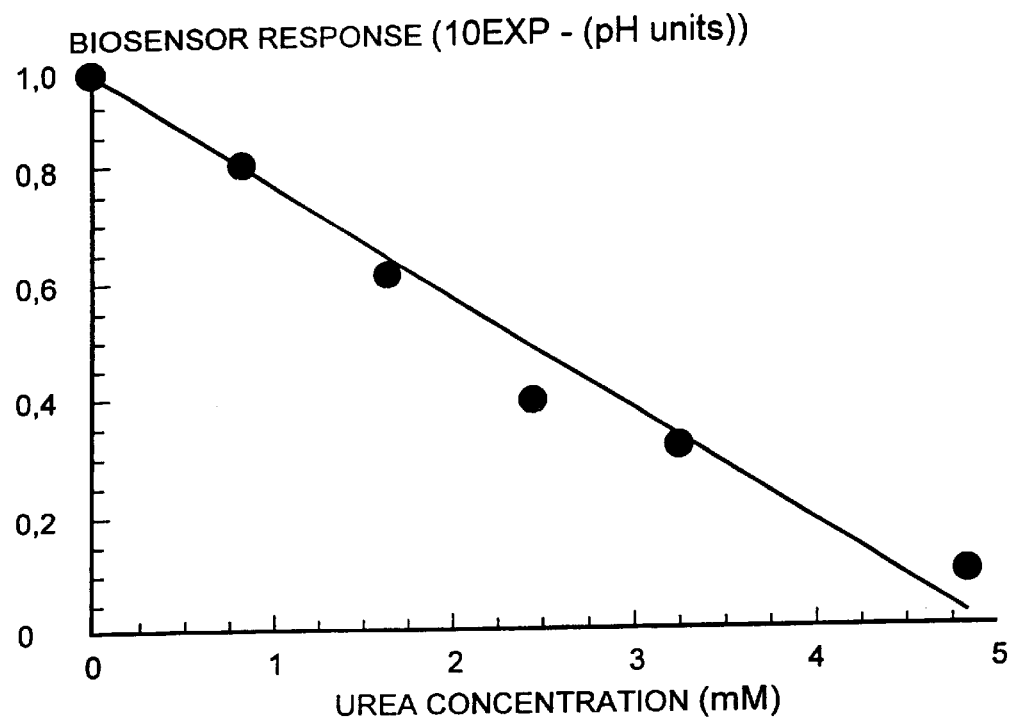
FIG. 3 is a graph showing the pH response of a urea biosensor according to the invention as a function of the urea concentration in a sample solution.

In order to exemplify the invention, a preliminary study has been made, in which a urea(bio)sensor has been constructed according to the principle described above, using a pH electrode as transducer means. As appears from FIG. 3, the pH response of the sensor correlates with the content of urea in the sample solution. The range of concentration is 0–5 mM, which is clinically relevant.

Furthermore, the effect of potential interfering substances, such as glucose, acetone, citric acid and sodium acetate, was investigated, see Table 2.

TABLE 2

| Substance | Concentration (mM) | Change in ΔpH (%) |
|---|---|---|
| Glucose | 28 | 0 |
| Acetone | 6.7 | 0 |
| Citric acid | 0.2 | 0 |
| Sodium acetate | 0.6 | 0 |
| Copper sulphate | 1 | −38 (0) |
|  | 2 | −65 (0) |

These did not have an effect on the pH response. It is a well-known fact that copper ions inhibit the catalytic ability of the used recognition element, the enzyme urea, and therefore a reduction of the pH response, when such ions were present in the sample solution, was no surprise. This effect could, however, be eliminated completely if a stabiliser reacting with the copper ions (for instance EDTA which forms a strong complex with the copper ions) was present, i.e. injected together with the enzyme.

Figure 4:
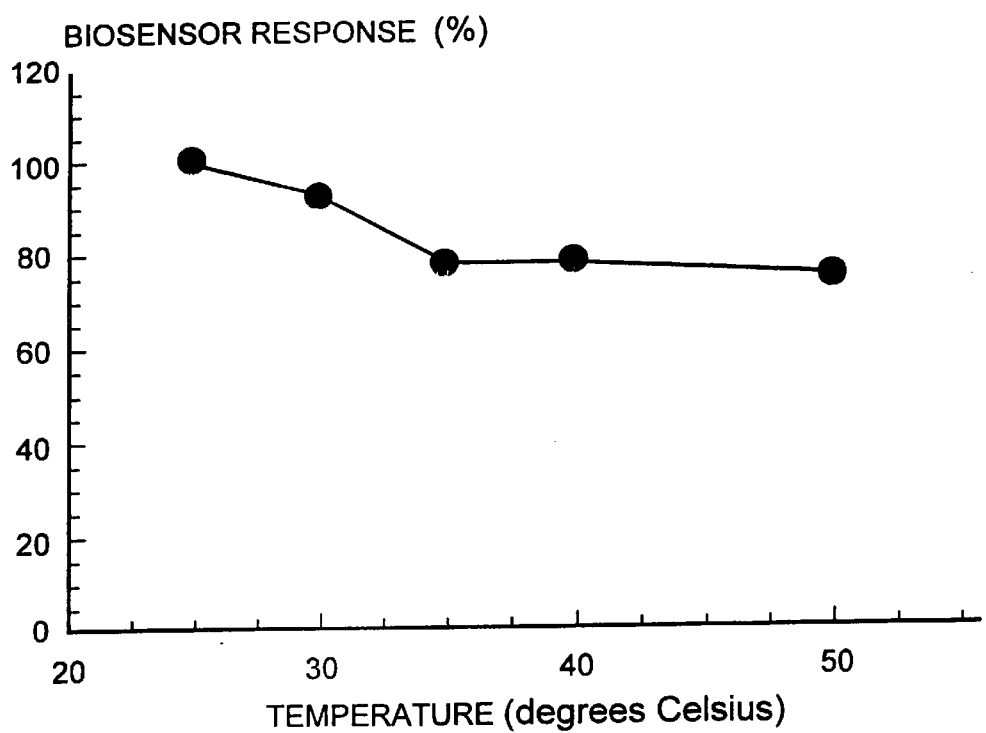
FIG. 4 is a graph showing the pH response of the urea biosensor according to the invention as a function of the temperature.

Finally, also the pH response of the urea(bio)sensor was analysed in measurements at increased temperatures, see FIG. 4. In these measurements, the sensor showed its superiority to conventional biosensors which are quickly deactivated at high temperatures, such as 50° C. In this case, only a 25% reduction of the pH response was noted.

EXAMPLE 2

In the present study, a biosensor with an injectible recognition element (glucose oxidase) was used to determine the glucose concentration in crude samples from a fermentation of a willow hydrolysate.

Materials and Methods

Yeast: Baker's yeast, *Saccharomyces cerevisiae* (Jästbolaget, Sweden) was used in the fermentation.

Preparation of the lignocellulosic hydrolysate: Willow, *Salix caprea*, was subjected to steam-pretreatment at 205° C. for 6 min [2]. The pretreated material was washed with water and filtered in a Larox filter press unit at a pressure of 14 bar. The cellulose fibres were hydrolysed in a stirred tank using Celluclast (20% w/w) and Novozyme (5% w/w) (Novo Nordisk, Denmark) for 90 h at 30° C., pH 4.8.

Fermentation: The lignocellulosic hydrolysate was supplemented with 2.5 g·l$^{-1}$ yeast extract, 0.25 g·l$^{-1}$ (NH$_4$)$_2$PO$_4$, 0.0025 g·l$^{-1}$ MgSO$_4$.7H$_2$O and 0.1 M NaPO$_4$, and inoculated to a final cell concentration of 6 g/l. The fermentation was run in a 22 l fermenter (Bioengineering, Switzerland) containing 16 l of medium at 30° C., pH 5.5, and a stirring speed of 300 rpm.

Biosensor measurements of glucose: The glucose concentration in samples taken out of the fermenter was measured, using a biosensor according to the invention. The mobile phase buffer used was a 0.1 M sodium phosphate buffer (pH 6.0) containing 0.15 M sodium chloride. The flow rate was set at 0.2 ml/min. The recognition element, glucose oxidase solution (1 mg/ml in mobile phase buffer) was injected into the mobile phase and when it reached the biosensor chamber, the flow was stopped. A current reading (ER) was recorded after 48 s. In addition, a background current reading (Br) was recorded, using the same procedure but injecting mobile phase buffer instead. The biosensor response was calculated as the difference (Er-Br) in the two current readings. The biosensor was calibrated with standard glucose solutions (0–50 g/l in mobile phase buffer). The fermenter samples were centrifuged (5 min at 1000 rpm) in order to remove the yeast cells and thus stop the consumption of glucose. Biosensor measurements were then performed on the undiluted samples.

HPLC analyses of glucose: Samples from the fermentation broth were filtered through 0.2 μm membrane filters (Sartorius, Germany) and analysed by HPLC (Shimadzu, Japan). Glucose and ethanol were separated at 45° C. using an Aminex HPX-87H column (Bio-rad, USA) and detected with a refractive index detector (Waters Millipore, USA). As the mobile phase 5 mM H$_2$SO$_4$ was used at a flow rate of 0.6 ml/min.

FIG. 5 shows the glucose concentration in the fermenter as a function of the fermentation time.

FIG. 6 shows a comparison of results obtained by the biosensor according to the invention (on undiluted samples) and results obtained by HPLC analysis (on diluted samples).

Results and Discussion

In contrast to HPLC measurements, the measurements carried out by the biosensor according to the invention are not influenced by interfering compounds present in the complex matrix of a lignocellulosic hydrolysate and thus the glucose concentration could be monitored in undiluted samples (FIG. 4). The recognition element, in this case glucose oxidase, is highly specific and responds only to the target analyte. A differential measurement method is used, allowing compensation for background currents which may arise from direct oxidation of sample components. No sample pretreatment was needed, the measurements were carried out in undiluted, unfiltered samples. Due to the fact that the yeast cells were not removed early enough before the measurements according to the invention, the glucose concentrations for each sample were slightly lower using this technique because of continuing fermentation than those obtained by HPLC analysis, where the samples were immediately filtered, for removal of cells (FIG. 5). After the measurements carried out by the sensor according to the invention, the HPLC analysis was repeated and the results confirmed the observed decrease in glucose concentration (data not shown). Whereas one HPLC analysis of an ethanolic fermentation takes at least 30 min for elution of all compounds present in the fermentation broth, the analysis time using the sensor according to the invention does not exceed 5 min, and no time is needed for regeneration of the sensor, which means that the analysis frequency can be very high. A very broad concentration range is covered by the sensor, which can detect concentrations down to 2 μM glucose. The sensor is suitable for in situ monitoring of fermentation processes. It can be sterilised in situ, and therefore the risk of contamination is minimised. Regeneration can be made if necessary during the fermentation by injection of a cleaning agent or by applying high potentials (±2V) to the electrode. No deactivation of the biological component will occur, as fresh enzyme solution (10 μl) is injected for every analysis. Automatisation of the analyses is easily accomplished by connection of an autoinjector to the electrode. At present, five different enzymes have been evaluated for use as recognition elements for the detection of urea, glucose, galactose, lactate and L-amino acids. Determination of several broth components will be possible by sequential injection of different enzymes.

To prove the utility of the invention for measurements in harsh chemical environments, the glucose content in orange juice, Coca Cola, Coca Cola Light and Pepsi Cola has been measured with excellent results.

What is claimed is:

1. A sensor, based on a dynamic initial change measuring process, for detecting an analyte in a solution, the sensor comprising:
    a working electrode;
    a selective membrane having first and second sides, the working electrode and the first side being spaced apart from each other to form a flow-through chamber therebetween;

an inlet to the chamber;

an outlet from the chamber;

a source of buffer;

a source of recognition element;

an injector connected to each of said sources for selecting the buffer or the recognition element;

a pump connected to injector for pumping the selected one of the buffer and the recognition element through the inlet, the chamber and the outlet;

the second side being in contact with the solution so that analyte passes through the membrane and reacts with the recognition element, and the working electrode generating a dynamic initial change signal proportional to the concentration of the analyte.

2. A sensor according to claim 1 wherein the working electrode is an electrochemical electrode.

3. A sensor according to claim 1 wherein the selective membrane is selected from the group consisting of ion exchange, gas permeable, group analyte selective hindering, and single analyte selective hindering membranes.

4. A sensor according to claim 1 wherein the recognition element is of biological origin.

5. A sensor according to claim 4 wherein the recognition element is catalytic.

6. A sensor according to claim 4 wherein the recognition element is non-catalytic.

* * * * *